(12) United States Patent
Vossgroene

(10) Patent No.: US 9,121,794 B2
(45) Date of Patent: Sep. 1, 2015

(54) PREPARATION DEVICE FOR MASS-SPECTROMETRIC SAMPLES

(71) Applicant: Bruker Daltonik GmbH, Bremen (DE)

(72) Inventor: Alexander Vossgroene, Bremen (DE)

( * ) Notice: Subject to any disclaimer, the term of this patent is extended or adjusted under 35 U.S.C. 154(b) by 73 days.

(21) Appl. No.: 13/969,990

(22) Filed: Aug. 19, 2013

(65) Prior Publication Data

US 2014/0056782 A1 Feb. 27, 2014

(30) Foreign Application Priority Data

Aug. 24, 2012 (DE) .......................... 10 2012 016 830

(51) Int. Cl.
| | | |
|---|---|---|
| *G01N 1/28* | (2006.01) | |
| *G01N 30/04* | (2006.01) | |
| *G01N 30/06* | (2006.01) | |

(52) U.S. Cl.
CPC . *G01N 1/28* (2013.01); *G01N 30/06* (2013.01)

(58) Field of Classification Search
None
See application file for complete search history.

(56) References Cited

U.S. PATENT DOCUMENTS

| | | | | |
|---|---|---|---|---|
| 4,849,176 A | * | 7/1989 | Sakagami | 422/64 |
| 5,039,614 A | * | 8/1991 | Dekmezian et al. | 436/43 |
| 5,110,098 A | * | 5/1992 | Merjanian | 269/21 |
| 5,575,176 A | * | 11/1996 | Rohrs et al. | 74/479.01 |
| 5,827,479 A | * | 10/1998 | Yamazaki et al. | 422/67 |
| 5,885,530 A | * | 3/1999 | Babson et al. | 422/65 |
| 5,944,476 A | * | 8/1999 | Bacchi et al. | 414/783 |
| 5,989,342 A | * | 11/1999 | Ikeda et al. | 118/52 |
| 6,323,035 B1 | | 11/2001 | Kedar et al. | |
| 6,448,066 B1 | * | 9/2002 | Wheatcroft | 435/287.2 |
| 6,450,218 B1 | * | 9/2002 | Andersson | 141/145 |
| 7,787,681 B2 | * | 8/2010 | Zhang et al. | 382/128 |
| 2002/0009394 A1 | | 1/2002 | Koster et al. | |
| 2002/0090320 A1 | | 7/2002 | Burow et al. | |
| 2002/0132353 A1 | * | 9/2002 | Tamura et al. | 436/43 |
| 2004/0163670 A1 | | 8/2004 | Ko et al. | |
| 2006/0263640 A1 | * | 11/2006 | Tamagaki et al. | 428/701 |
| 2008/0227663 A1 | * | 9/2008 | Tisone et al. | 506/39 |
| 2009/0180931 A1 | * | 7/2009 | Silbert et al. | 422/63 |
| 2009/0268194 A1 | * | 10/2009 | Tomita | 356/39 |
| 2011/0070654 A1 | * | 3/2011 | Tokhtuev et al. | 436/100 |
| 2012/0079875 A1 | * | 4/2012 | Nogami et al. | 73/61.59 |
| 2012/0160665 A1 | * | 6/2012 | Ramm et al. | 204/192.38 |

OTHER PUBLICATIONS

Tu, T and Gross, M. Miniaturizing sample spots for matrix-assisted laser desorption. Trends Analyt Chem; 2009; 28(7). pp. 833-841.*

(Continued)

*Primary Examiner* — Jill Warden
*Assistant Examiner* — Benjamin Whatley
(74) *Attorney, Agent, or Firm* — Robic, LLP

(57) ABSTRACT

Devices for the preparation of a plurality of samples on mass-spectrometric sample supports are presented, where the samples are prepared by the application of liquids such that they are suitable for ionization in a mass spectrometer, for example ionization by matrix-assisted laser desorption (MALDI). The invention proposes that the dispenser and sample sites are positioned with respect to each other by means of two rotations about two eccentric axes. As acids and aggressive solvents are used, which have to evaporate on the samples, the preparation can be carried out in a closed chamber with air circulation, filter, dispenser and mounting table for the sample support. Drives for positioning the dispenser and sample support relative to each other are preferably kept outside the chamber because aggressive vapors would very quickly damage the motors and the complex cross-rails of the XY translation stages used to move the sample supports.

17 Claims, 3 Drawing Sheets

(56) References Cited

OTHER PUBLICATIONS

Waters Controlling contamination; (see attached pdf http://web.archive.org/web/20100501000000*/http://www.waters.com/webassets/cms/support/docs/715001307d_cntrl_cntm.pdf; published online Jun. 2010. retrieved using the wayback archive http://archive.org/web/ using website: http://www.waters.com/webassets/cms/support/docs/715001307d_cntrl_cntm.pdf).*

* cited by examiner

PREPARATION DEVICE FOR MASS-SPECTROMETRIC SAMPLES

BACKGROUND OF THE INVENTION

1. Field of the Invention

The invention relates to devices for the preparation of a plurality of sample sites on mass spectrometric sample supports, where samples are prepared with liquids in such a way that they are suitable for ionization in a mass spectrometer, for example ionization by matrix-assisted laser desorption (MALDI).

2. Description of the Related Art

The preparation of samples for ionization by matrix-assisted laser desorption (MALDI) requires aggressive organic solvents to dissolve the matrix material, and to apply the solutions to the sample support manually or with the aid of pipetting robots. The solvent must subsequently be vaporized to allow the growth of crystals of the matrix substance, into which likewise dissolved analyte substances are embedded. Since ionization by matrix-assisted laser desorption (MALDI) is widely known, no detailed description will be given here.

Nowadays, the mass-spectrometric identification of microbial samples involves daily preparation of many thousands of samples in microbiological laboratories for ionization by matrix-assisted laser desorption. Since only the substances from inside the microbes are useful for the mass-spectrometric identification, the cells of the microbes must first be cell disrupted. Often this also takes place on the sample support. The first step here is to apply small, hardly visible quantities of around $10^5$ to $10^7$ microbes from agar plate colonies onto the sample sites of the sample support. The cells of the microbes are usually cell disrupted by strong acids, which must subsequently be dried up by vaporization. Seventy percent formic acid (boiling point 101° C.; vapor pressure 43 hPa at 20° C.) or trifluoroacetic acid of similar concentration (TFA; boiling point 72° C.; vapor pressure 110 hPa at 20° C.) is usually used for this purpose. Quantities of around one microliter are applied onto each sample; once the acid is almost dried up, the matrix solution is applied, also in quantities of around one microliter. The matrix solution usually contains a solid organic acid (usually α-cyano-4-hydroxycinnamic acid, HCCA, but also 2,5-dihydroxybenzoic acid, DHB, for example) in a solvent mixture of acetonitrile and alcohols, for safety reasons usually ethanol, although methanol would be the better alternative. The matrix solution penetrates into the microbes through the weakened cell walls, causing them to burst and dissolving the soluble contents. The microbes are then identified with the aid of a mass spectrum of the contents.

The sample supports are usually the size of microtitration plates (or a fraction thereof) and nowadays usually have 96 or 384 visible sample sites for the application and preparation of the samples. Sample supports with 1536 sample sites are also in use. The sample sites with diameters of 0.8 to 2.0 millimeters can be identified with the aid of milled-in rings, where the milled edges prevent the applied acids and solvents from flowing away; the sample sites can also take the form of hydrophilic areas in a hydrophobic environment.

At present, the preparation is still mostly carried out manually with dispensing pipettes, without a hood (fume cupboard) because hoods are rare in microbiological laboratories. This can be hazardous to health if the ventilation is insufficient. Even when a hood is available, it is often not used because pipetting in an open hood is very awkward. So there has long been a need for an automatic preparation device which facilitates the application of the acids and matrix solutions, does not release hazardous vapors, and preferably does not require a hood.

The liquid quantities of around one microliter do not drip from the pipette tip of their own accord, but must be applied according to the Prior Art by dabbing them onto the sample. A new pipette tip must be used for each sample in order to prevent samples being transferred. Non-contact application of the liquids onto the samples would therefore be particularly advantageous because it would eliminate the need to replace the pipette tips each time.

For non-contact application it is advantageous to position the dispenser exactly vertically above the sample sites. Automatic preparation thus requires the provision of movement devices which can bring the dispenser and the sample sites precisely in line vertically. Since the evaporating acids and solvents attack surfaces, especially metal surfaces in sliding contact, the usual cross slides driven by stepper motors and screw threads (as with an X-Y translation stage) cannot be used.

This disclosure references ionization by matrix-assisted laser desorption (MALDI), in which ions are produced during the desorption process initiated by laser beam pulses. It goes without saying, however, that sample preparations shall also be possible where the analyte substances in the prepared samples can be transferred into the gaseous phase regardless of their ionization. The type of ionization can be selected as required to suit the application. Simple laser desorption in combination with chemical ionization (LDCI) can be carried out, for example, or direct electrospray ionization from the surface (DESI), but other types of ionization can also be used. Accordingly, the term "ionization with matrix-assisted laser desorption" must not be understood as a restriction.

Furthermore, this disclosure occasionally mentions the application of a drop onto a sample. It is understood that the dispensed drop can also be applied to an uncoated sample site of the sample support, for example as a preparatory step for the subsequent coating with a microbial sample. Accordingly, embodiments of this type, also, must not be deemed to be in any way restrictive.

In view of the foregoing, there is a need for a device which can automatically prepare the sample sites on mass-spectrometric sample supports with liquids for a later ionization of the samples, for example for an ionization by matrix-assisted laser desorption, with strongly reduced effect of released vapors on the movement devices. It is preferable if the device is designed in such a way that the user cannot be endangered by the vapors given off either.

SUMMARY OF THE INVENTION

The invention proposes that the dispenser for liquids and the sample sites on a sample support are positioned with respect to each other by means of two rotations about two eccentric axes. For example, the dispenser can be mounted on a swiveling arm and moved over the sample sites located on a sample support table, which can also swivel. Or the dispenser can be stationary, and the sample sites on the sample support can be moved under the dispenser by a coupled motion system with two eccentric rotations. As acids and aggressive solvents are used, which have to evaporate on the samples, it is preferable to carry out the preparation in a closed chamber with air circulation, air filter, dispenser and mounting table for the sample support. The driving motors for positioning the dispenser and sample support relative to each other are preferably kept outside the chamber with axis tightened by sealing means, such as O-rings, because the aggressive vapors would very quickly damage the motors. Complex cross-rails of XY translation stages to move the sample supports are avoided, because they create hard-to-solve tightening problems.

The invention is characterized by a special design of the positioning devices, which does not require linear sliding motions, and thus has no slide rails, threads or other elements that are susceptible to corrosion and have relatively large and easily damaged surfaces. A dispenser on a swiveling arm, moved by a first drive, and a sample support table, swiveled by a second drive, can be moved in such a way that the dispenser is located vertically above an arbitrarily selected sample site on the sample support table, for example. Or the dispenser can be stationary, and each sample site of the sample support can be moved under the dispenser by a coupled motion system with two eccentric rotations. Techniques for applying the liquids onto the sample sites in small amounts with the aid of dispensers which are vertically above the sample sites and which operate without contact are known in principle and can be used here. The chamber for preparing the sample sites must preferably be separated from the chamber containing the electromechanical drives (drive motors) for positioning dispenser and sample sites with respect to each other. This separation can be achieved by a chamber wall or other type of shield, for example. The forces required for positioning dispensers relative to sample sites can be transmitted via shafts through sealed openings in the chamber wall into the chamber where the preparation is performed.

Several dispensers for several different types of liquid can also be mounted in this system. Furthermore, sensors can be present for monitoring the correct application of the liquids. This not only allows sample sites to be prepared for the subsequent application of samples; it is particularly possible to prepare samples which have already been applied to sample sites. The samples can be simple chemical analyte samples; more particularly they can be small quantities of microbes which are to be identified by mass spectrometry. The microbe cells must be cell disrupted for this identification, and require special preparation with strong acids for this purpose. Auxiliary devices can be used to automatically wash each dispenser in the event of malfunctions, for example if matrix substance crystallizes at the tip of the dispenser; and the cleaning fluid is then disposed of. If a chamber is used as the preparation space, it is preferably equipped with filters and air circulation for controlled drying of the liquids on the sample sites. It then does not need to be standing in a hood, and there are no hazards for the user.

The preparation device according to the invention saves time and material compared to manual preparation. The time factor for the identification of microbes is particularly important in medical diagnostics because it can save lives and shorten the length of the illness. Compared to today's still quite primitive preparation of samples, particularly of microbe samples, more intelligent methods can be used which make it possible to obtain good mass spectra from only $10^3$ instead of $10^5$ microbes with the aid of better preparation methods, for example. Although the preparation time is then longer, the time saved on culturing would be far greater.

DETAILED DESCRIPTION

While the invention has been shown and described with reference to a number of embodiments thereof, it will be recognized by those skilled in the art that various changes in form and detail may be made herein without departing from the spirit and scope of the invention as defined by the appended claims.

The invention is characterized by a special design of the positioning devices for the dispenser and the sample support, which in the different embodiments is characterized by two eccentric rotational movements in each case, as depicted in FIGS. 1 to 4 in particular. The positioning device can be located in a hermetically sealed chamber with filters and air circulation, for example. Techniques for applying the liquids onto the sample sites by means of dispensers which are vertically above the sample sites and operate without contact are known in principle and can be used here. The forces required for the relative positioning of dispensers and sample sites can be transmitted into the preparation chamber as torques via shafts which pass through sealed openings in the chamber wall. The invention is particularly characterized by the fact that it does not require linear sliding motions in the preparation chamber, and thus has no slide rails, threads or other elements with large gliding surfaces which are susceptible to corrosion.

For the non-contact dispensing of the small quantities of liquid onto the sample sites, there are different types of technical solution, such as piezo dispensers. As can be seen in a part of FIG. 5, it is particularly simple and advantageous to have a dispenser unit (50) which has two concentric capillaries (52). A tiny pump presses a drop (60) of around one microliter out of the central capillary; a small pressure surge of air or another gas suitable for this purpose from the surrounding capillary then strips the hanging drop (60) from the central capillary and causes it to drop onto the sample site. The pressure surge of gas and also the impinging speed of the drop must be small enough that the drop does not splatter. The non-contact deposition of the liquid drops means that replaceable pipette tips are no longer required for the preparation.

Figure 1:
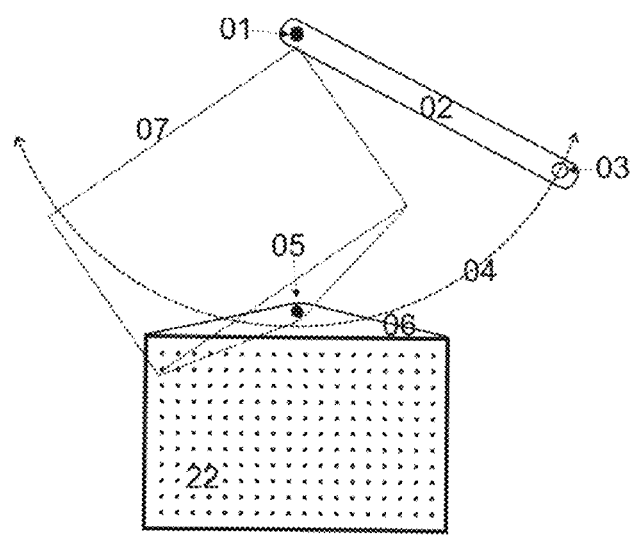
FIG. 1 shows, on the one hand, a swiveling arm (02) with dispenser (03), which can be rotated about the axis (01) along the arc (04). On the other hand, the figure shows a sample support table (06), which is largely hidden by a sample support plate (22) placed on the table, and which can be rotated about the axis (05) in such a way that, in combination with a rotation of the swiveling arm for the dispenser, every sample site (dark spots) on the sample support (22) can be positioned under the dispenser (03). The sample support table at position (07) shows the minimum separation which is required between the two axes of rotation (01) and (05) if both rotations are to be fed through a chamber wall from below.

In a first embodiment of the invention, a dispenser (03) is mounted on a swiveling arm (02), as shown in FIG. 1, and can be guided over each sample site on a sample support plate (22) located on a sample support table (06), which also swivels. The guidance is achieved by using the shafts (01) and (05) to set the two rotating positions accordingly. The shaft (01) for the swiveling arm (02) can enter the chamber from the top; the shaft (05) for the sample support table from below; it is also possible to feed in both shafts from below, however. The liquids and gases which are required for the dispensing can be fed in by tubes or small pipes routed through a hollow shaft (01), for example. It is also possible to mount several dispensers (03) for different liquids on the swiveling arm (02), and also sensors for the correct deposition of the liquids. This embodiment of the invention is particularly simple.

Figure 5:
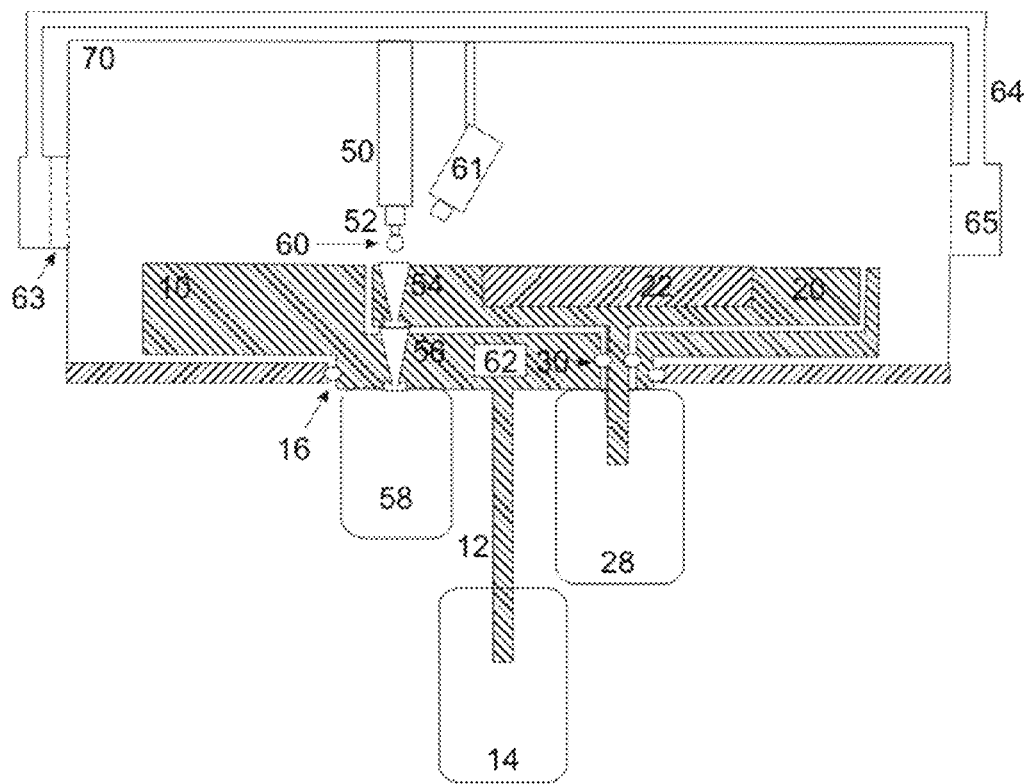
FIG. 5 shows schematically an example of a possible design for a chamber (70) with two eccentric turntables according to FIGS. 2 to 4. As shown in the previous FIGS. 2 to 4, any sample site on the sample support (22) can be accurately positioned under the dispenser (50) by rotating the turntables (10) and (20). A pressure surge can be used to place a suspended drop (60) from a fixed dispenser (50) with concentric capillaries (52) onto a randomly chosen sample site without any contact. The rotations of the turntables (10) and (20) are effected by the motors (14) and (28), for example stepper motors with a built-in reduction gear. The shafts for transmitting the torques are sealed by the sealing rings (16) and (30) and move on bearings so that the turntables can move freely and without friction (except for the friction in the seals). The arrangement also contains two waste funnels (54) and (56) in the turntables (20) and (10), which are one above the other when the two turntables are in a home position, as depicted in FIG. 2, for example. The two waste funnels (54) and (56) are shaped so that the rinsing liquid drips or flows immediately into the next funnel without being able to get into the gap between the two turntables. A waste container (58) is fastened under the turntable (10). This arrangement serves to rinse and clean the dispenser if its functioning is impaired by crystallizing matrix material, for example. Correct dispensing may be controlled by a sensor (61), here a mini-camera. The turntable (10) can be heated by an element (62), housing a heater and a temperature sensor, with cables (not shown) running through shaft (12). Air from the chamber (70) can be cleaned by filter (63), warmed up within channel (64), and returned into the chamber (70) by blower (65).

A second embodiment operates with a fixed dispenser (50), as shown in FIG. 5, and only the sample sites on the sample support (22) are moved in order to position them under the dispenser (50) by means of a simple movement system with two eccentric rotations. Since the movement of the sample support (22) is to be effected without a large mechanical system which is susceptible to corrosion, the sample support (22) is located on a turntable (20), which is mounted eccentrically on or in a larger turntable (10) so that it can be rotated.

Figure 2:
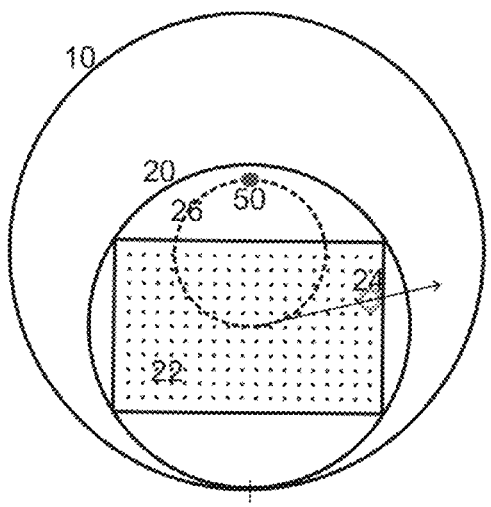
FIGS. 2 to 4 show how, by using two eccentric turntables (20) and (10), a randomly chosen sample site (24) on the sample support (22) can be positioned underneath a fixed dispenser (50). From the starting position in FIG. 2, the first, small turntable (20), as shown in FIG. 3, is first rotated through the angle $\phi_{20}$ so that the selected sample site (24) comes to lie on the broken circle (26). This broken circle (26) is arranged concentrically with respect to the axis of the second, large turntable (10) and the radius represents the separation of the dispenser (50) from the axis of rotation of the large turntable (10). By rotating the second, large turntable (10) through the angle $\phi_{10}$ (FIG. 4) and taking with it the first, small turntable (20), the sample site (24) can now be positioned under the dispenser (50).
Figure 3:
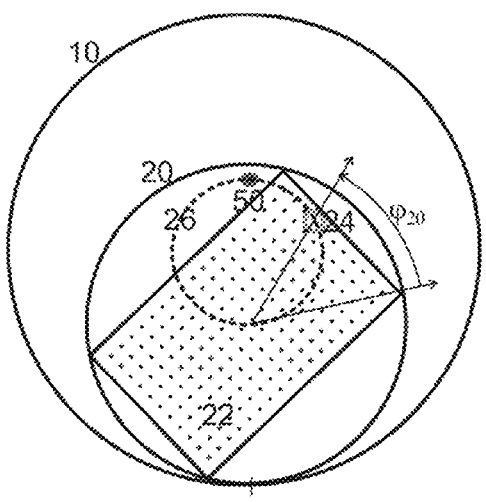
Figure 4:
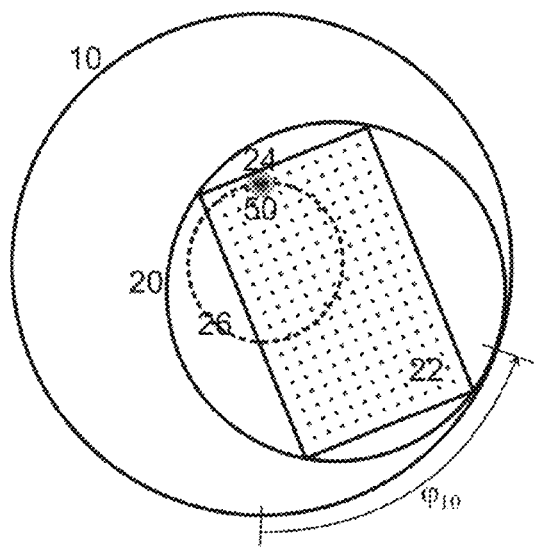

By rotating the two turntables, any sample site of the sample support (22) can be moved under the preparation dispenser (50), as depicted in FIGS. 2 to 4. The sample support (22) can be inset into the turntable (20) in order to provide a level surface for a stream of drying air. It is then preferable if the contour of a recess in the turntable (20) is adapted to the dimensions of the sample support (22). The turntables (10) and (20) are rotated by the motors (14) and (28), which can be stepper motors. The stepper motors can be equipped with reduction gears, encoder disks and limit switches.

For embodiments with a fixed dispenser it is advantageous to keep their liquid and gas feeds short. Short feeds do not require large quantities of liquid to fill the supply lines, which particularly facilitates the rinsing and cleaning work. The small dimensions also prevent pressure drops in the gas, which could lead to the gas pressure surge for stripping a droplet from the capillary not being strong enough. Furthermore, with a fixed dispenser, the starting procedure for a dispensing of the droplet by squeezing it from the dispenser capillary can be carried out while the turntables are still in motion. With this design there is no longer a danger of the droplet being shaken off prematurely due to the deceleration of the rotational movement of the dispenser, nor a danger of the droplet executing oscillating movements, which could make it more difficult to strip it off onto the sample site, or would require a period of attenuation.

FIGS. 2 to 4 schematically depict how a randomly chosen sample site (24) on the sample support (22) can be positioned under the dispenser (50) with the aid of the two turntables (10) and (20). From the starting position in FIG. 2, the small turntable (20) is first rotated through the angle $\phi_{20}$ so that the sample site (24) comes to lie on the broken circle (26), as shown in FIG. 3. This broken circle (26) is arranged so as to be concentric to the large turntable (10). By rotating the large turntable (10) through the angle $\phi_{10}$, and taking the small turntable (20) with it, the sample site (24) can now be positioned exactly under the dispenser (50). Since the geometry of the arrangement is known in detail, the required angles of rotation $\phi_{20}$ and $\phi_{10}$ can be easily calculated mathematically by a control program. These calculations become particularly simple if the radius of the broken circle (26), which represents the distance of the dispenser (50) from the axis of the large turntable (10), corresponds precisely to the distance between the axes of the two turntables. The diameter of the circle (26) must be at least as large as half the greatest distance between the sample sites on the sample support (22). It is also possible for the calculations to be carried out only once and then stored in a table. These calculations comprise the absolute angles of rotation $\phi_{20}$ and $\phi_{10}$ for all the sample sites, calculated from the home position, or the relative angles of rotation, calculated from the last sample site approached. In order to save time, the two rotational movements can naturally be carried out simultaneously or at least with a partial temporal overlap.

The rotational movements of the two turntables can be limited, to plus/minus 180° or slightly less, for example. Limit switches can then be incorporated for these limits. Limiting the motion in this way allows rotating parts, such as the stepper motor (28) in FIG. 5, to also be provided with electrical connections without using sliding contacts.

The precision necessary to set the angles of rotation $\phi_{20}$ and $\phi_{10}$ can also be calculated from geometric considerations for a specified positional precision. The precision required then determines the gear reduction at the stepper motors (14) and (28), and the step size of the stepper motors. In order to ensure reproducible setting of the positions without mechanical hysteresis, the rotational movements can also be pretensioned in one direction by springs; or the movements into a preparation position can always be done from the same direction, if necessary by initially overrunning the target position and then moving back.

The fixed dispenser (50) and the movement device with the two turntables (10) and (20) are preferably positioned in a hermetically sealed chamber (70), while the drive motors, gears and encoder disks are outside the chamber in order to protect them from the aggressive vapors. Possible arrangements with sealing rings (16, 30) are shown in FIG. 5 for the sealing of the shafts which transmit the torques into the interior of the chamber (70). The sealing rings can take the form of O-rings, for example, but radial shaft seals with sealing lips are also well-suited. The feedthrough for the "shaft" of the large turntable (10) with sealing ring (16) must be very large, however, so this seal should have a loose sealing lip in order not to obstruct the rotational movement too much.

It is also possible to design the gap between the large turntable (10) and the chamber floor in such a way that instead of, or in addition to, the sealing ring (16), it can be at least partially filled with a low viscosity oil of extremely low vapor pressure. Commercial diffusion pump oil is particularly suitable. Diffusion pump oil is extremely resistant to oxidation and ageing and has a hardly measurable vapor pressure at the temperatures used. It is kept in the gap by the capillary effect and its lubricating properties facilitate the rotational movement. The separation in the gap can be maintained by gliding pads of low frictional resistance, if required. The same applies to the gap between the large turntable (10) and the small turntable (20). The oil also serves particularly to seal the chamber in order to prevent the ingress of corrosive vapors into the space containing the sensitive motors (14, 28). These can be oleophobically coated at the edges, with oleophobic amino acids, for example, so that the oil cannot run out. It is also possible to close the gaps at the edges by gluing on strips of a blotting paper or thin felt.

It should be noted here that, within the scope of the invention, an embodiment is also possible where two eccentric turntables, whose shafts extend into the chamber from above, could move a dispenser mounted thereon over the sample sites on a stationary sample support. This embodiment is not explained in more detail here, however.

Figure 6:
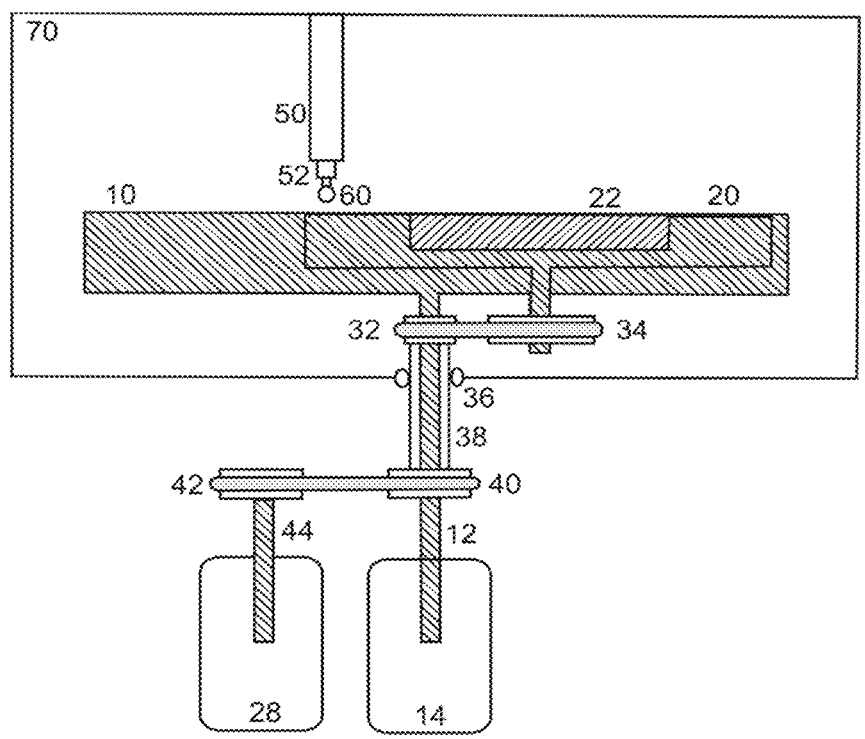
FIG. 6 is a schematic depiction of a slightly different chamber design with the positioning device for dispenser and sample support table according to the invention. Here too, any sample site on the sample support (22) can be accurately positioned under the preparation dispenser (50) by rotating the small turntable (20) and the large turntable (10). The rotation of the large turntable (10) by the motor (14) is effected directly here by the relatively thin shaft (12), while the rotation of the small turntable (20) is effected indirectly by the motor (28) with built-in reduction gear via the two belt drives (40/42) and (32/34) and the hollow shaft (38) with sealing ring (36), which is concentric to the shaft (12). The belt drives can be replaced by gear sets in order to improve the precision. The gear set is best made of a dimensionally stable and solvent-resistant, chemically inert plastic, such as polyimide. This arrangement has a belt drive or gear set in the preparation chamber, but is covered by the basic idea of the invention due to its exclusive use of rotational drives.

A further embodiment shall be described here briefly, which is depicted in FIG. 6 and shows a schematic representation of a slightly different design of the movement devices in the preparation chamber. In this case, also, any sample site of the sample support (22) can be accurately positioned under the preparation dispenser (50) by rotating the small turntable (20) and the large turntable (10). While the rotation of the large turntable (10) is effected directly by motor (14) via the relatively thin shaft (12), the rotation of the small turntable (20) is effected indirectly by the motor (28), with built-in reduction gear, via the two belt drives (40/42) and (32/34) and the hollow shaft (38) with sealing ring (36), which is concentric to the shaft (12). The belt drives can be replaced by a gear set in order to improve the precision. The gear set in the preparation chamber is best made of a dimensionally stable and solvent-resistant, chemically inert plastic, such as polyimide.

It is advantageous for all embodiments which have a chamber (70) as the preparation volume to be provided with optional gas circulation and filters (not shown here). The chamber can then be designed as part of a bench-top instrument which does not have to be placed in a hood (fume cupboard). The filters can be simple carbon filters in standard sizes, for example. The filtered gas, such as lab air, from which solvents, acids and excess moisture have been removed, is then fed in again in such a way that it flows slowly over the surface of the sample support in order to dry samples. The humidity of the circulating gas can also be controlled. The chamber can be provided with a lid, which can be opened manually in order to insert the sample supports. For safety reasons, the lid should automatically close when it is released. The lid then also serves as a safety measure to protect against explosions: if a mixture of solvent and air explodes, the lid lifts slightly and lets the explosion gases escape, thus preventing the chamber from being destroyed.

For a more rapid vaporization of the liquids, it is expedient to be able to heat the sample support table (06), the turntable (10) and, additionally or alternatively, the turntable (20), to a specified temperature, for example to 40° C. by means of a built-in heating element with temperature sensor. The electric cables for the heating current and the temperature sensors can be fed through the shaft (12), for example, which must be hollow for this purpose. On the other hand it is also possible to heat the current of circulating gas accordingly.

Several dispensers for several different types of liquid can also be present in this system. Although not necessary, it is nevertheless particularly favorable if the different dispensers are all located on the broken circle (26) of FIGS. 2 to 4. In addition, sensors which monitor the proper application of the liquid can be installed on this circle or at other locations of the device. Such a sensor can take the form of a mini-camera, for example, whose images can be evaluated visually or automatically. It is also possible to use probes which measure the electric capacitance to the sample site or scattered light reflected from the sample site.

The dispensers have to be cleaned from time to time in order to remove interfering residues, for example crystallized matrix material. Crystallized matrix material at the edge of the central dispenser capillary leads to the drops no longer being stripped off vertically. The capillary can be cleaned by flushing it with pure solvent, for example. As shown in FIG. 5, the two turntables (20, 10) can incorporate two waste funnels (54) and (56) which are precisely one above the other when the two turntables are in a home position, as depicted in FIG. 2, for example. The two waste funnels (54) and (56) are best shaped so that the rinsing liquid drips or flows immediately into the next funnel without being able to get into the gap between the two turntables. A waste container (58) is fastened under the turntable (10). The cleaning of the dispenser can also be assisted by a brush which is installed in a fixed position on the turntable (10), next to the funnel (54), and which brushes the nozzle from below with the aid of a slight to and fro rotation of one of the two turntables. During rinsing, the solvent runs off into the waste container (58). The waste container can be equipped with a pump (not shown here) in order to pump off the rinsing liquid.

With this device for the preparation of sample sites on sample supports, it is possible to prepare sample sites for the subsequent application of samples, and it is especially possible to prepare samples which have already been applied to sample sites. The samples can be simple chemical analyte samples, but in particular they can be small quantities of microbes which are to be identified by mass spectrometry. The microbe cells must be cell disrupted for this identification and, as described above, require special preparation with strong acids for this purpose.

Now the implementation of a manual method will be briefly described, which is often used nowadays for the MALDI preparation of microbe samples on a sample support with the aid of a device which is designed according to the principles of this invention. After manually lifting the chamber lid, a fully prepared sample support can be removed and exchanged for a sample support which is freshly coated with samples. The sample support is recessed into the small turntable (20), but can be lifted out with finger grip holes (not shown in the Figures) or with special tools. The sample support is brought to the desired temperature within only a few minutes. The microbe samples, which are already on selected sites on the sample support, are now each contactlessly sprinkled with around one microliter of formic acid, sample by sample. The samples can be coated row by row, for example, in order to keep the movement distances small and thus save time. Other sequences can also be optimal, however, for example coating in quadrants. A sample can be moved and coated in around half a second; all the samples of a sample support with 384 samples are therefore completely coated with formic acid in around 3.2 minutes. This time is sufficient to digest the microbe cells; the cell walls will at least be weakened to such an extent that they can be made to burst by osmosis by the time the matrix solution is being applied. If the heating temperature is chosen correctly, by the time the last sample has been applied, the first sample has dried sufficiently for the solution of the matrix material to be applied. It takes another 3.2 minutes to apply matrix material to all the samples (in the same sequence). If a further five minutes are calculated for the final drying with crystallization of the matrix substance, only 15 minutes or so are needed to prepare the 384 samples, including initial heating; around four sample supports can therefore be prepared per hour. If the coatings are checked with sensors, it must be expected that this will take longer, but here too, one sample support takes half an hour at most to prepare.

The preparation device according to the invention saves time in comparison to manual preparation. It also saves pipette tips. In medical diagnostics, not only the cost factor but also the time factor for the identification of unknown microbes is especially important because early identification of the microbes can save lives and shorten the duration of illnesses significantly.

Only the preparation method commonly used today was implemented in the brief description of the preparation method for microbe samples with the device according to the invention. However, it is also conceivable that, compared to today's still quite primitive microbe preparation, more intelligent methods can be used which allow good mass spectra to be obtained from only $10^3$ instead of $10^5$ microbes, by increasing the ion yield in the mass spectrometer, for example. Although the preparation time is then longer, the time saved on culturing would be far greater.

Today, there is, for example, discussion about whether the proteins released during the cell digestion cannot be bound firmly to protein-adsorptive layers, such as dinitrocellulose layers, and then be rinsed with water in order to remove salts, but also other substances which hinder the ionization ("inhibitors"), before the matrix solution is applied. A simple rinsing dispenser can consist of an outer capillary to feed in the rinsing water and an inner capillary to remove the rinsing water by suction. The rinsing dispenser is located at a mere half a millimeter or so above the sample to be rinsed. Since the rinsing is always carried out with fresh rinsing water, there is no need to worry that proteins will be transferred in this process. It is also possible to rinse with liquids other than water, in order to remove fatty acids, for example. In this way the preparation chamber with the device according to the invention can not only be used for preparation methods commonly employed today, but also allows more complex methods to be carried out in the future which are hard to carry out manually, possibly with the installation of further dispensers or even sensors, where necessary.

Of course, the device according to the invention also allows the preparation of sample supports on which not all the sample sites are coated with samples. The positions coated with samples must be notified to the control program for this purpose.

The positioning of the sample support with the aid of two rotational movements, as presented in this disclosure, may represent an opportunity to move away from the rectangular designs of sample supports known from the Prior Art (and also shown in the Figures) and to choose round designs adapted to the rotations instead. For example, instead of the usual matrix arrangement of the sample sites on the sample support in rows and columns, it may be useful to adopt an arrangement on imaginary circles with different diameters, concentric to the axis of rotation of the turntable, or alternatively on an imaginary spiral curve which runs from the edge to the center of the sample support and has the axis of rotation of the turntable as its center. A particular feature is that the sample sites can be arranged along an imaginary line from the center of the circle to the circumference at the same angular positions, but on different radii. A person skilled in the art will easily be able to use geometric considerations in order to find a particularly advantageous design of sample support.

Within the framework of this disclosure, the terms "eccentric" and "eccentric rotational movements" are used to mean that the two (essentially parallel) axes of rotation for positioning the sample support table and dispenser relative to each other are arranged at a distance from each other. They do not mean that the elements rotating about these axes, such as swiveling arm or turntables, must have a design which is rotationally symmetric relative to these axes (albeit such a design can be advantageous in some cases for production reasons or for reasons of mass equilibrium, for example).

What is claimed is:

1. A device for preparing samples for ionization in a mass spectrometer, comprising:
   a table for receiving a sample support having a plurality of sample sites, the table comprising a first turntable and a second turntable mounted eccentrically on or in the first turntable, the sample support being located on the second turntable and the turntables being eccentrically connected as to provide for a coupled motion wherein rotating the first turntable moves the second turntable, but rotating the second turntable does not move the first turntable;
   a dispenser for dispensing liquids onto sample sites of the sample support on the table, the dispenser being installed in a fixed position so that it does not rotate; and
   drives, connected to the turntables, for positioning the dispenser and the sample support table relative to each other by rotational movements of the turntables about two eccentric axes;
   wherein the rotational movements of the turntables allow any sample site of the sample support to be positioned under the dispenser.

2. The device according to claim 1, wherein the turntables have a drain for rinsing fluid, which is used to clean a dispenser tip of the dispenser, and a waste container positioned such that it can receive the rinsing fluid when the two turntables are moved into a home position.

3. The device according to claim 1, wherein at least one of the turntables is equipped with a heating system to supply heat to the sample support.

4. The device according to claim 1, wherein the dispenser is designed for a non-contact dispensing of droplets of a defined size onto the sample sites.

5. The device according to claim 1, further comprising more than one dispenser.

6. The device according to claim 1, further comprising sensors to control application of liquid to a correct sample site on the sample support.

7. The device according to claim 1, wherein the drives for the rotational movements comprise stepper motors and are equipped with at least one of reduction gear, encoder disks, and limit switches.

8. The device according to claim 1, wherein the
table for receiving the sample support and the dispenser for dispensing liquids onto sample sites of the sample support on the table are located in a sealable chamber; and
wherein the drives with associated shafts for effecting a relative positioning of the dispenser and the sample sites on the sample support with respect to each other by eccentric rotational movements are arranged outside the chamber and the shafts transmit driving forces therefrom into the chamber through a sealed chamber wall opening.

9. The device according to claim 8, wherein the chamber is provided with a gas circulation means for controlled drying of liquids on the sample sites and associated filters for removing at least one of solvents, acids and excess moisture from gas to be filtered.

10. The device according to claim 1, wherein the first turntable is larger than the second turntable.

11. The device according to claim 10, wherein the second turntable has a recess for receiving the sample support.

12. The device according to claim 10, wherein a distance between the dispenser and the axis of the first turntable corresponds to a distance between the axes of the two turntables.

13. The device according to claim 6, wherein the sensors are at least one of a mini-camera, an electric capacitance probe and a scattered light probe.

14. The device according to claim 1, wherein the sample support has a rectangular or round shape.

15. The device according to claim 1, wherein the rotational movements are pre-tensioned in one direction by springs in order to ensure a reproducible setting of sample site position without mechanical hysteresis.

16. A device for preparing samples for ionization in a mass spectrometer, comprising:
a table for receiving a sample support having a plurality of sample sites, the table being installed in a fixed position so that it does not rotate;
a first turntable and a second turntable mounted eccentrically on or in the first turntable so as to provide for a coupled motion between the turntables, the coupled motion being such that rotating the first turntable moves the second turntable, while rotating the second turntable does not move the first turntable;
a dispenser for dispensing liquids onto sample sites of the sample support on the table, the dispenser being mounted on the second turntable; and
drives, connected to the turntables, for positioning the dispenser and the sample support table relative to each other by rotational movements of the turntables about two eccentric axes;
wherein the rotational movements of the turntables allow the dispenser to be positioned above any sample site of the sample support.

17. The device according to claim 1, wherein the rotational movements are always done from the same direction by initially overrunning a target position and then moving back in order to ensure a reproducible setting of sample site position without mechanical hysteresis.

* * * * *